United States Patent
Jensen et al.

(10) Patent No.: US 11,633,551 B2
(45) Date of Patent: Apr. 25, 2023

(54) GASEOUS NITRIC OXIDE DELIVERY SYSTEM AND METHODS OF USE

(71) Applicant: Hansen Pharmaceutical, LLC, South Miami, FL (US)

(72) Inventors: Jeffrey L. Jensen, Phoenix, AZ (US); Jason R. Hanft, Coral Gables, FL (US); Steve Jensen, Boston, MA (US)

(73) Assignee: Hansen Pharmaceutical, LLC, South Miami, FL (US)

( * ) Notice: Subject to any disclaimer, the term of this patent is extended or adjusted under 35 U.S.C. 154(b) by 530 days.

(21) Appl. No.: 16/773,676

(22) Filed: Jan. 27, 2020

(65) Prior Publication Data

US 2020/0230330 A1    Jul. 23, 2020

Related U.S. Application Data

(63) Continuation-in-part of application No. 16/506,786, filed on Jul. 9, 2019, now abandoned, which is a
(Continued)

(51) Int. Cl.
*A61M 13/00* (2006.01)
*A61M 35/00* (2006.01)
*A61K 33/00* (2006.01)

(52) U.S. Cl.
CPC ............ *A61M 13/00* (2013.01); *A61K 33/00* (2013.01); *A61M 35/30* (2019.05);
(Continued)

(58) Field of Classification Search
CPC .................. A61M 13/00; A61M 35/30; A61M 2202/0275; A61M 2202/20;
(Continued)

(56) References Cited

U.S. PATENT DOCUMENTS 6,432,077 B1    8/2002    Stenzler
6,793,644 B2    9/2004    Stenzler
(Continued)

FOREIGN PATENT DOCUMENTS

WO    0030659 A1    6/2000
WO    2010014848 A1    2/2010

OTHER PUBLICATIONS

International Search Report and Written Opinion issued in PCT/US2015/060461, dated Feb. 10, 2016, 21 pages.
(Continued)

*Primary Examiner* — Amber R Stiles
(74) *Attorney, Agent, or Firm* — Polsinelli PC; Roberta J. Hanson

(57) ABSTRACT

Embodiments of the present disclosure provide systems and devices for delivering gaseous Nitric Oxide (gNO) under therapeutic parameters to reduce infection in a subject. Certain embodiments include devices and systems for delivering pressurized gNO to reduce bioburden and promote healing in the wounds of subjects having various disease conditions, including skin and soft tissue infections (SSTIs) and osteomyelitis. In some embodiments, the present disclosure provides portable wound healing devices for delivering pressurized gNO to the site of a wound to treat various disease conditions in a subject. Other embodiments relate to systems and devices for delivering and for monitoring gaseous Nitric Oxide (gNO) under therapeutic parameters of use to treat a subject. In certain embodiment, the devices include a subject interface unit comprising sensors for detecting gNO pressure and/or gNO flow.

22 Claims, 8 Drawing Sheets

Related U.S. Application Data continuation of application No. 14/939,995, filed on Nov. 12, 2015, now Pat. No. 10,391,266.

(60) Provisional application No. 62/079,461, filed on Nov. 13, 2014.

(52) U.S. Cl.
CPC . *A61M 2202/0275* (2013.01); *A61M 2202/20* (2013.01); *A61M 2202/203* (2013.01); *A61M 2202/206* (2013.01); *A61M 2205/3327* (2013.01)

(58) Field of Classification Search
CPC ...... A61M 2202/203; A61M 2202/206; A61M 2205/3327; A61K 33/00
See application file for complete search history.

(56) References Cited

U.S. PATENT DOCUMENTS

| | | | |
|---|---|---|---|
| 7,520,866 B2 | 4/2009 | Stenzler et al. | |
| 7,892,198 B2 | 2/2011 | Stenzler | |
| 9,364,388 B2 | 6/2016 | McCaney et al. | |
| 2002/0155164 A1 | 10/2002 | Figley et al. | |
| 2005/0191372 A1 | 9/2005 | Stenzler et al. | |
| 2007/0083316 A1 | 4/2007 | Kurz et al. | |
| 2007/0088316 A1* | 4/2007 | Stenzler | A61M 35/30 604/23 |
| 2008/0029093 A1 | 2/2008 | Stenzler et al. | |
| 2008/0193566 A1 | 8/2008 | Miller et al. | |
| 2009/0216204 A1 | 8/2009 | Bhavaraju et al. | |
| 2011/0245759 A1 | 10/2011 | McCaney et al. | |
| 2012/0283626 A1* | 11/2012 | Belson | A61M 35/30 604/23 |
| 2013/0018300 A1 | 1/2013 | Igney et al. | |
| 2014/0088490 A1* | 3/2014 | McCaney | A61F 13/00063 604/24 |
| 2016/0081876 A1 | 3/2016 | McCaney et al. | |
| 2016/0137968 A1 | 5/2016 | Packert et al. | |

OTHER PUBLICATIONS

Franz T J: "Percutaneous absorption on the relevance of in vitro data", Journal of Investigative Dermatology, Nature Publishing Group, US, vol. 64, No. 3, Mar. 1, 1975 (Mar. 1, 1975), pp. 190-195, KP003002651, ISSN: 0022-202X, DOI: 10.1111/1523-1747. EP12533356.

Bandarage et al., "Nitric Oxide-Releasing Nonsteroidal Anti-inflammatory Drugs: Novel Gastrointestinal-Sparing Drugs," Mini Rev Med Chem, Jan. 2001:57-70.

Bauer et al., "Evaluation of linear polyethyleneiminelnitric oxide adduct on wound repair: therapy versus toxicity," Nound Repair Regen, Jun. 1996:569-77.

De Groote et al., "NO Inhibitions: Antimicrobial Properties of Nitric Oxide," Clin Infect Dis, 1995, 21(suppi2):S162-164.

Delledonne et al., The Functions of Nitric Oxide-Mediated Signaling and Changes in Gene Expressing During Hypersensitive Response: Antioxidants & Redox Signaling vol. 5, No. 1, 2003 pp. 33-41.

Fang, "Mechanisms of Nitric Oxiderelated Antimicrobial Activity," Amer Soc Clin Invest, 1997, 33:2818-25.

Frank "Large induction of the chemotactic cytokine RANTES during cutaneous wound repair: a regulatory role for citric oxide in keratinocyte-derived RANTES expression," Biochem J, 2000, 347 Pt 1: 265-73.

Ghaffari A et al: "A direct nitric oxide gas delivery system for bacterial and mammalian cell cultures", Nitric Dxide: Biology and Chemistry, Academic Press, Amsterdam, NL, vol. 12, No. 3, May 1, 2005 (May 1, 2005), pp. 129-140, XP027227858, ISSN: 1089-8603.

Hardwick et al. "A novel method for the delivery of nitric oxide therapy to the skin of human subjects using a semipermeable membrane," Clinical Sci, 2011, 100:395-400.

Hickey "Role of inducible nitric oxide synthase in the regulation of leucocyte recruitment," Clin Sci, 2001, 100:1-12.

International Search Report and Written Opinion issued in PCT/US2015/060426, completed Mar. 4, 2016, 13 pages.

Klevens, et al., "Invasive methicillin-resistant *Staphylococcus aureus* infection in the United States," 2007, JAMA, 298: 1762-177.

Livermore, "Of Pseudomonas, porins, pumps and carbapenems," J Antimicorb Chemotherapy, 47:247-250; 2001.

Miller "Nitric Oxide: The Future is Bright," Journal for Respiratory Care Practitioners, Oct. 2003: 10-12.

Moncada et al., "Nitric Oxide: Physiology, Pathophysiology, and Pharmacology," Pharmacal Rev, 1991,43:10942.

Moran et al., "Methicillin-resistant *S. aureus* infections among patients in the emergency department," 2006, N. Engl. J. Med., 355:666-674.

Omerod et al., The Inflammatory and Cytotoxic Effects of a Nitric Oxide Releasing Cream on Normal Skin, J Invest Dermatol, 1999, 113:392-7.

Oplander et al: "Dermal Application of Nitric Oxide In Vivo: Kinetics, Biological Responses, and Therapeutic Potential In Humans", Clinical Pharmacology and Therapeutics, vol. 91, No. 6, May 2, 2012 (May 2, 2012), pp. 1074-1082, KP055251651, US, ISSN: 0009-9236, DOI: 10.1038/clpt.2011.366.

Pankey, 2005, "In vitro synergy of ciprofloxacin and gatifloxacin against ciprofloxacin-resistant Pseudomonas aeruginosa," Antimicrob Agents Chemotherapy, 49:2959-2964.

Paramythiotou et al., "Acquisition of multidrug-resistant Pseudomonas aeruginosa in patients in intensive care units: role of antibiotics with antipseudomonal activity," 2004, Clin Infect Dis, 38:670-7.

Patel et al. "Biological aspects of reactive nitrogen species," Biochim Biophys Acta, 1999, 1411:385-400.

Shabini "Enhancement of wound repair with a topically applied nitric oxide-releasing polymer," Wound Repair Regen, Apr. 1996:353-63.

Vasquez-Torres et al., "Therapeutic Applications of Nitric Oxide in Infection," Nitric Oxide and Infection, 1999, 475-88.

Weller et al., "A randomized trial of acidified nitrite cream in the treatment of tinea pedis," J. Am Acad Dermatol, 1998, 38:559-63.

Witte et al., "Role of nitric oxide in wound repair," Amer Journal of Surg, 2002, 183:406-412.

\* cited by examiner

FIG. 8A
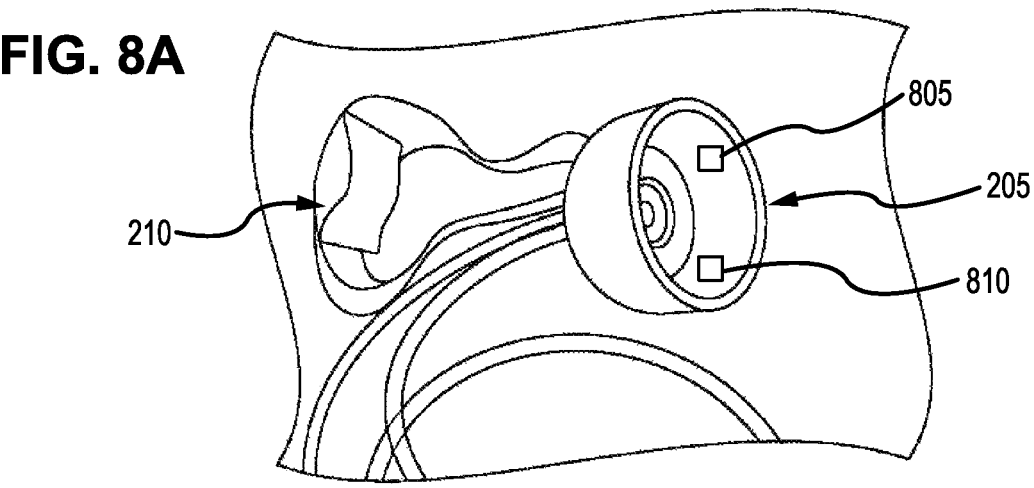
FIG. 8B
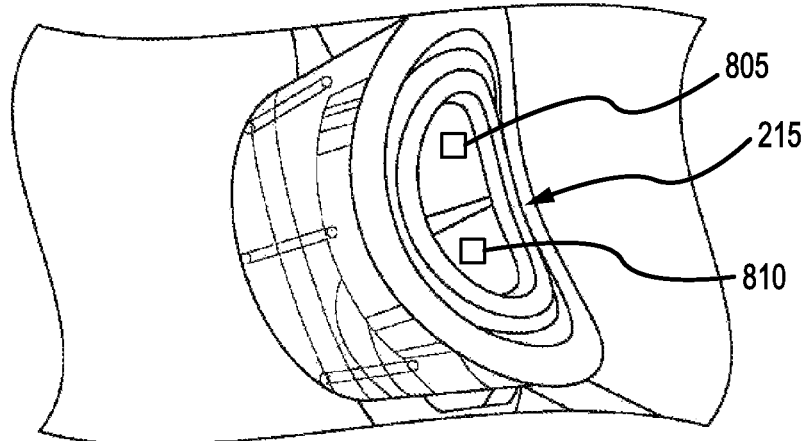
FIG. 8C
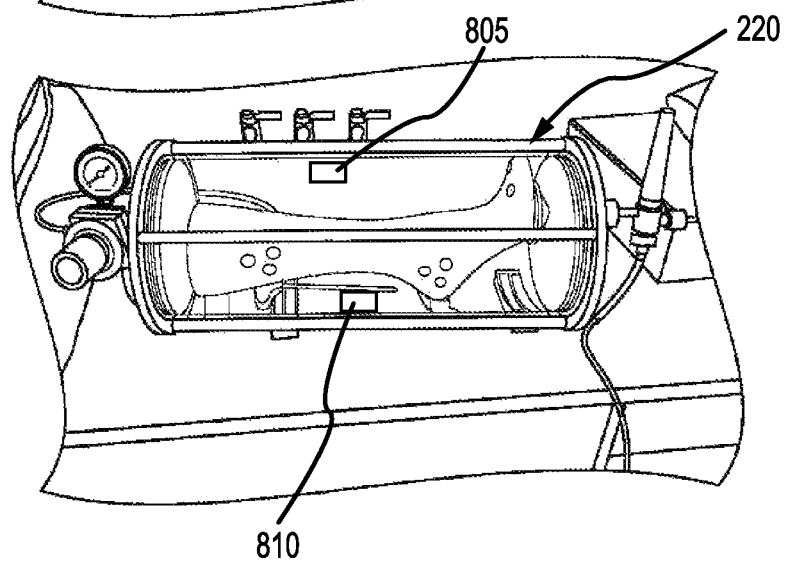
FIGS. 8A - 8C

GASEOUS NITRIC OXIDE DELIVERY SYSTEM AND METHODS OF USE

RELATED APPLICATIONS

This continuation-in-part application claims the benefit of continuation application U.S. patent application Ser. No. 14/506,786 filed Jul. 9, 2019, which claims the benefit of U.S. patent application Ser. No. 14/939,995 filed Nov. 12, 2015 issued on Aug. 27, 2019 as U.S. Pat. No. 10,391,266, which claims the benefit of U.S. Provisional Patent Application Ser. No. 62/079,461, filed Nov. 13, 2014. These applications are incorporated herein by reference in their entirety for all purposes.

STATEMENT REGARDING FEDERALLY FUNDED RESEARCH

Embodiments disclosed herein have been supported in part by Defense Advanced Research Projects Agency (DARPA), DARPA Grant No. HR 0011-11-1-0006. The government has certain rights to this invention.

FIELD

Embodiments of the present disclosure provide systems and devices for delivering gaseous Nitric Oxide (gNO) under therapeutic parameters to reduce a targeted infection in a subject. Certain embodiments include devices and systems for delivering pressurized gNO to reduce bioburden and promote healing in the wounds of a subject having one or more health conditions, including, but not limited to, skin and soft tissue infections (SSTIs) and/or osteomyelitis. Some embodiments disclosed herein relate to reducing pathogenic infections in soft tissue of a subject in order to promote wound healing in persistent or chronic wounds. Other embodiments relate to systems and devices for delivering and for monitoring gaseous Nitric Oxide (gNO) under therapeutic parameters of use to treat a subject.

BACKGROUND

Nitric Oxide (NO) is a ubiquitous small molecule messenger involved in many pathological and physiological processes. NO plays critical roles in vascular and neuronal signal transduction pathways, smooth muscle contractility, bioenergetics, platelet adhesion and aggregation, immunity, and cell death regulation. NO deficiency is implicated in many pathophysiological processes such as hypertension, cardiovascular dysfunctions, neurodegeneration, arthritis, asthma and septic shock. gNO is one of the few gaseous signaling molecules known and is additionally exceptional due to the fact that it is a radical gas. It is a known byproduct in almost all types of organisms, ranging from bacteria to plants, fungi, and animal cells.

There are several mechanisms by which gNO has been demonstrated to affect the biology of living cells. These include oxidation of iron-containing proteins such as ribonucleotide reductase and aconitase, activation of the soluble guanylate cyclase, ADP ribosylation of proteins, protein sulfhydryl group nitrosylation, and iron regulatory factor activation. NO has also been demonstrated to activate NF-κB in peripheral blood mononuclear cells, an important transcription factor in iNOS gene expression in response to inflammation. Additionally, during an immune response, NO is secreted as free radicals and is toxic to many bacteria and intracellular parasites; NO causes DNA damage and degradation of iron sulfur centers into iron ions and iron-nitrosyl compounds.

The administration of exogenous NO not only constitutes a powerful way to supplement NO when a subject cannot generate enough for normal biological functions, it also offers a means for accelerating wound healing and reducing bioburden in a subject. NO produced by both iNOS and eNOS plays many important roles in wound healing, from the inflammatory phase through to scar remodeling. In particular, NO exerts cytostatic, chemotactic, and vasodilatory effects during early wound repair, regulates proliferation and differentiation of several cell types, modulates collagen deposition and angiogenesis, and affects wound contraction. However, the timing, concentration, pressurization, and site of gNO administration are all poorly understood critical factors affecting the ability of gNO to facilitate wound repair.

SUMMARY

Embodiments of the present disclosure provide systems and devices for delivering gaseous Nitric Oxide (gNO) under therapeutic parameters to reduce a targeted infection or treat a wound in a subject. Certain embodiments disclosed herein include devices and systems for delivering pressurized gNO to reduce bioburden and promote healing in the wounds of a subject having one or more health conditions, including, but not limited to, skin and soft tissue infections (SSTIs) and/or osteomyelitis. Some embodiments disclosed herein relate to reducing pathogenic infections in soft tissue of a subject in order to promote wound healing in persistent or chronic wounds.

Embodiments of the present disclosure provide a gaseous nitric oxide (gNO) delivery device for delivering pressurized gNO to a subject. In some embodiments, the device includes a source of gNO functionally coupled to a subject interface unit, a gas flow regulator that measures flow rate of the gNO and a gas pressure regulator that measures pressure of the gNO as the gNO is delivered through the subject interface unit to the subject, wherein the gNO treats an infection in the subject.

In certain embodiments, the pressure of the gNO delivered to the subject is from about 0.15 ATM to about 1.0 ATM.

In other embodiments, the gNO is delivered to the subject at a flow rate from about 0.1 liters/minute to about 1.0 liters/minute.

In some embodiments, the concentration of the gNO delivered to the subject is about 1.0% to about 2%. In certain embodiments, the concentration of the gNO delivered to the subject is 2% or less. In yet other embodiments, the concentration of gNO is 1.75% or less; or 1.5% or less or 1.25% or less.

In certain embodiments, the gNO can be delivered to the subject continuously. In other embodiments, the gNO can be delivered to the subject continuously for about 15 minutes to about 120 minutes. In yet other embodiments, the gNO can be delivered to the subject intermittently for about 15 minutes to about 120 minutes using a programmed treatment or a manned treatment regimen. It is contemplated that the treatment duration on an intermittently delivered regimen can vary regarding the length of time for administering the gNO and the length of time between where no gNO is being administered to the subject. Parameters for intermittent administration can depend on the subject to be treated and/or the location of an affected site as well as the condition of the subject (e.g. diabetes and a diabetic ulcer, an infected wound).

In yet other embodiments, a device can further include one or more nitric oxide sensors.

In some embodiments, the device can further include one or more oxygen sensors.

In yet other embodiments, a device can further include a gas flushing mechanism or capturing mechanism to reduce the incidence of or prevent the subject from being exposed to gNO when the subject interface unit is removed from the subject. In some embodiments, a capturing mechanism contemplated herein is capable of capturing excess gNO when the subject interface unit is removed from the subject.

In some embodiments, the subject interface unit includes a gas inlet to ensure continuous flow of the gNO and continuous exposure of gNO to the subject. In other embodiments, a gas outlet can be used to ensure intermittent flow of gNO to the subject.

In certain embodiments, the subject interface unit includes an attachment mechanism for maintaining a seal on the subject (or an area of a subject's appendage) while the gNO gas is being delivered.

In other embodiments, treating the infection in the subject includes reducing bioburden in a wound located on the subject.

In some embodiments, treating the infection in the subject can include reducing one or more symptom(s) associated with the infection.

In certain embodiments, treating the subject includes reducing the risk of developing an infection from exposure to one or more pathogenic organisms in the subject by pre-exposing them to gNO prior to onset of an infection at a wound site. In accordance with these embodiments, a subject can be treated with gNO upon presentation of a new wound or during or after a surgical procedure.

In other embodiments, the infection includes an area of the subject's body infected by at least one pathogen selected from the group consisting of a bacterium, a virus, a fungus, a parasite, an arthropod, a protozoan, and an antibiotic resistant bacterium, or a combination thereof.

In some embodiments, the infection is located in or surrounding a lesion, including, but not limited to, a surgical wound, a trauma wound, a burn, an abscess, an actinic keratosis, a keloid, a scar, and skin cancer and a combination thereof.

Embodiments of the present disclosure also include a gaseous nitric oxide (gNO) delivery system for delivering pressurized gNO to a subject. In some embodiments, the system includes a source of gNO functionally coupled to a subject interface unit, a gas flow regulator that measures flow rate of the gNO and a gas pressure regulator that measures pressure of the gNO as the gNO is delivered through the subject interface unit to the subject, wherein the gNO treats, prevents the onset of, or reduces the onset of, an infection in the subject.

In certain embodiments according to systems disclosed herein, the pressure of gNO delivered to the subject is from about 0.15 ATM to about 1.0 ATM, wherein the flow rate of the gNO delivered to the subject is from about 0.1 liters/minute to about 1.0 liters/minute, and wherein the concentration of the gNO delivered to the subject is about 1.0% to about 2%. In certain embodiments, the concentration of the gNO delivered to the subject is 2% or less. In yet other embodiments, the concentration of gNO is 1.75% or less; or 1.5% or less or 1.25% or less.

In other embodiments, the system disclosed herein includes one or more oxygen, nitric oxide, or nitric dioxide sensors.

In certain embodiments, treating an infection in the subject using a system disclosed herein comprises reducing bioburden (e.g., pathogenic organisms) in a wound on the subject.

In other embodiments, a system disclosed herein can further include a gas flushing mechanism or a gas capturing mechanism to reduce the chances of or prevent the subject from being exposed to gNO when the subject interface unit is removed.

In certain embodiments, the subject interface unit includes a gas outlet to ensure continuous or intermittent flow of the gNO and continuous or intermittent exposure of gNO to the subject.

Embodiments of the present disclosure also include a method of treating a wound on a subject. In some embodiments, the method includes attaching a subject interface unit to a wound site on the subject, the subject interface unit functionally coupled to a source of gaseous nitric oxide (gNO), and delivering an effective amount of gNO to the wound site on the subject, wherein the gNO treats the wound site on the subject.

In certain embodiments, the pressure of the gNO delivered to the wound site on the subject is from about 0.15 ATM to about 1.0 ATM, wherein the flow rate of the gNO delivered to the wound site on the subject is from about 0.1 liters/minute to about 1.0 liters/minute, and wherein the concentration of the gNO delivered to the wound site on the subject is about 1.0% to about 2%.

In some embodiments, the gNO is delivered to the wound site on the subject continuously or intermittently for about 15 minutes to about 120 minutes or more; for example, depending on the site to be treated.

In other embodiments, treating the wound site includes reducing bioburden in an infection in the wound site.

In certain embodiments, treating the wound site comprises reducing the risk of developing an infection in the wound site.

As used herein, the terms "subject," "user," and/or "patient" can include humans and other animals or mammals that are in need of treatment and capable of using or have assisted use of devices and systems as described herein. Additionally, the terms "subject," "user," and/or "patient" can include humans and other mammals treated in any type of environment such as a clinical setting, non-clinical setting, experimental setting, etc. In embodiments, a user may be incapable of effectively operating the various gNO delivery systems and may require the assistance of a third party. As such, functions performed by the "user" can include functions performed by a third-party provider, such as a healthcare provider and/or another authorized person associated with the user.

The terms "determine," "calculate," and "compute," and variations thereof, as used herein, are used interchangeably and include any type of methodology, process, mathematical operation or technique.

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

(FIG. 5A: wounded, uninfected tissue; FIG. 5B: tissue wounded and infected for 3 hours; and FIG. 5C: tissue wounded and infected for 24 hours)

(FIG. 6A is stained with Hematoxylin and eosin; FIG. 6B is stained with Feulgen reaction; FIG. 6C is stained with Modified Congo Red; FIG. 6D is stained with Modified Congo Red with Carbol Fuchsin; FIG. 6E is stained with PAS; FIG. 6F is stained with Calcofluor)

FIGS. 8A-8C represent exemplary subject interface units that couple to the gNO delivery device having pressure and flow sensors, according to embodiments of the present disclosure.

Figure 1:
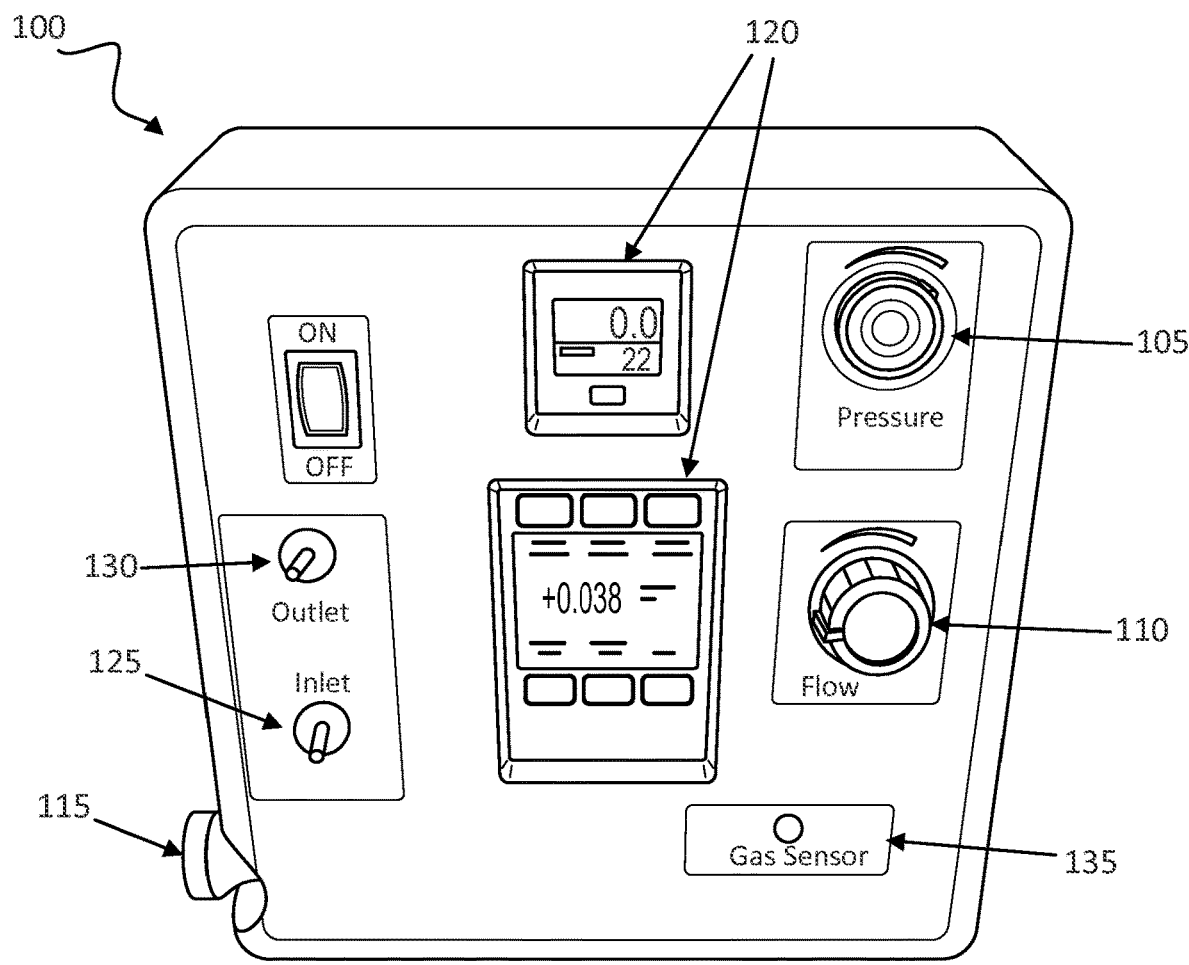
FIG. 1 is a representation of a portable gaseous Nitric Oxide (gNO) delivery device, according to an embodiment of the present disclosure.

While the disclosure is amenable to various modifications and alternative forms, specific embodiments have been illustrated by way of example in the drawings and are described in detail below. The intention, however, is not to limit the disclosure to the particular embodiments described. On the contrary, the disclosure is intended to cover all modifications, equivalents, and alternatives falling within the scope of the disclosure and/or the claims.

DETAILED DESCRIPTION

Embodiments of the present disclosure provide systems and devices for delivering gaseous Nitric Oxide (gNO) under therapeutic parameters to reduce infection in a subject. Certain embodiments include devices and systems for delivering pressurized gNO to reduce bioburden and promote healing in the wounds of subjects having various disease conditions, including skin and soft tissue infections (SSTIs) and osteomyelitis.

FIG. 1 is a representation of a portable gNO delivery device, according to an embodiment of the present disclosure. The portable gNO delivery device of the present disclosure can include a housing unit 100 as for example, a control unit, that includes, but is not limited to, a gas pressure regulator 105, a gas flow regulator 110, and a subject interface unit. The gNO delivery devices and systems disclosed herein allow for easy transport of the device to various settings or regions where therapeutic intervention is not amenable to an in-patient hospital or other centralized setting. As illustrated in FIG. 1, gas housing unit 100 used with gNO delivery devices and systems of the present disclosure can include various features to control the delivery of gas to a subject (e.g., gas housing units from ALICAT SCIENTIFIC). For example, gas housing units used with the portable gNO delivery devices and systems of the present disclosure can include a port for inserting a power source 115 and/or a port for inserting one or more rechargeable battery units (not illustrated), various digital readouts for gas concentration and pressure 120, various gas inlets 125 and outlets 130, and various gas concentration sensors 135. Alternatively, a gas housing unit 100 can include a gas inlet operably linking a gas source (not shown) to the gas housing unit 100. In other embodiments, a gas housing unit can further include a programmable system for continuous, intermittent or a combination of delivery methods (not shown). For example, intermittent delivery can be pre-programmed to correlate with the specifics of an infection or wound for optimal delivery and treatment of the subject. In another exemplary gas housing unit 100, sensor receivers can be included in 100 to receive feedback from one or more of a pressure sensor and a flow sensor in order to receive signals from the one or more of pressure sensor and flow sensor and regulate flow and pressure of the gas. In certain embodiments, the one or more of pressure sensor and flow sensors are operably linked to the gas housing unit 100 from a subject interface unit (not shown) and the one or more of pressure sensor and low sensors transmit signals to the gas housing unit, for example for regulation of pressure and flow of the gas to the subject interface unit. Gas housing unit 100 used with the portable gNO delivery devices and systems of the present disclosure can be functionally coupled with the subject interface unit to facilitate the administration of gNO to a subject. Various type and models of gas housing units can be used to deliver pressurized gNO to a subject, as would be recognized by one or ordinary skill in the art based on the present disclosure.

In some embodiments, the portable gNO delivery devices of the present disclosure include a source of gNO, such as a gNO storage container that houses the gNO prior to delivery to a subject. The gNO storage container can be any suitable tank or cylinder that contains medical grade compressed gNO for delivery to a subject. Suitable gNO storage cylinders can also be equipped with pressure gauges or regulators, flow gauges or regulators, adjustments knobs for adjusting both outlet pressure and flow rates, gas inlets/outlets, and the like. In some aspects, the gNO cylinder can include a specific amount of gNO (e.g., liters of gNO), such that the delivery of the gNO to a subject having a certain condition constitutes a single treatment. For example, a gNO storage cylinder can contain approximately 9.0 liters of gNO for example, when it is delivered to a subject for 90 continuous minutes at a flow rate of 0.1 liters per minute (LPM), the gNO will be exhausted. In other embodiments, a gNO storage cylinder can contain a predetermined amount of gNO for example, when it is delivered to a subject intermittently for a predetermined treatment time and a predetermined flow rate (e.g. 0.1 liters per minute (LPM) when delivering gas to the subject), the gNO will be exhausted. In this manner of operation, the gNO storage cylinder can function as a safety feature to prevent gNO overexposure to the subject.

In some embodiments, the gNO delivered to a subject is part of a gas mixture that has a concentration of gNO that ranges from about 1 ppm to about 1500 ppm, from about 1000 ppm to about 5000 ppm, from about 4000 ppm to about 10,000 ppm, from about 9,000 ppm to about 16,000 ppm, from about 15,000 ppm to about 22,000 ppm, from about 21,000 ppm to about 28,000 ppm, from about 27,000 ppm to about 34,000 ppm, and from about 33,000 ppm to about 40,000 ppm. In some aspects, the gNO delivered to the subject is 10,000 ppm, or about 1.0% of the gas mixture (1 ppm is about 0.0001%).

In some embodiments, the gNO delivery device is equipped to deliver gNO under various parameters, including delivering gNO at various pressures. In some aspects, gNO can be delivered to a subject at pressures anywhere between about 0 atmospheres (ATM) to about 1 ATM (i.e., the pressure within the subject interface unit, above atmosphere). The delivery of gNO to a subject in this range is independent of, and in addition to, the pressure of the external environment (e.g., barometric pressure). As would be recognized by one of ordinary skill in the art based on the present disclosure, units of pressure can be expressed using various metrics, including ATMs, pounds-force per square inch (e.g., lbf/in$^2$ or psi), bar (e.g., Mbar, kilobar, millibar, etc.), pascal (e.g., Pa, kPa, MPa, etc.) and/or torr (e.g., Torr, mTorr, etc.). For example, 1 ATM can be expressed as 14.695 psi. In some aspects of the present disclosure, pressure can be measured and expressed in increments that are tenths, hundredths and/or thousandths of these various metrics. In some aspects, the gNO is delivered at various ranges. For example, the gNO gas can be delivered at pressures from about 0 ATM to about 1.0 ATM, from about 0 ATM to about 0.9 ATM, from about 0 ATM to about 0.8 ATM, from about 0 ATM to about 0.7 ATM, from about 0 ATM to about 0.6 ATM, from about 0 ATM to about 0.5 ATM, from about 0 ATM to about 0.4 ATM, from about 0 ATM to about 0.3 ATM, from about 0 ATM to about 0.2 ATM, and from about 0 ATM to about 0.1 ATM. In some aspects, the gNO can be delivered at pressures from about 0.1 ATM to about 0.5 ATM, from about 0.15 ATM to about 1.0 ATM, from about 0.15 ATM to about 0.5 ATM, from about 0.15 ATM to about 0.25 ATM, and from about 0.25 ATM to about 0.5 ATM. In some aspects, the gNO can be delivered at pressures of about 0.1 ATM, about 0.15 ATM, about 0.2 ATM, about 0.25 ATM, about 0.3 ATM, about 0.35 ATM, about 0.4 ATM, about 0.45 ATM, about 0.5 ATM, about 0.55 ATM, about 0.6 ATM, about 0.65 ATM, about 0.7 ATM, about 0.75 ATM, about 0.8 ATM, about 0.85 ATM, about 0.9 ATM, and about 0.95 ATM.

Figure 2A:
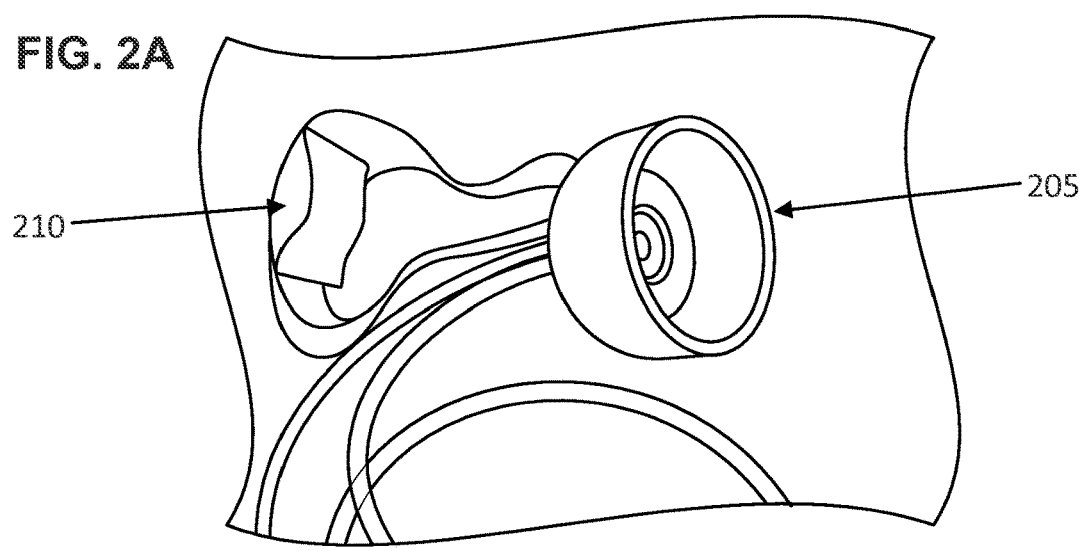
FIGS. 2A-2C are representations of three subject interface units that couple to the NO delivery device, according to embodiments of the present disclosure.
Figure 2B:
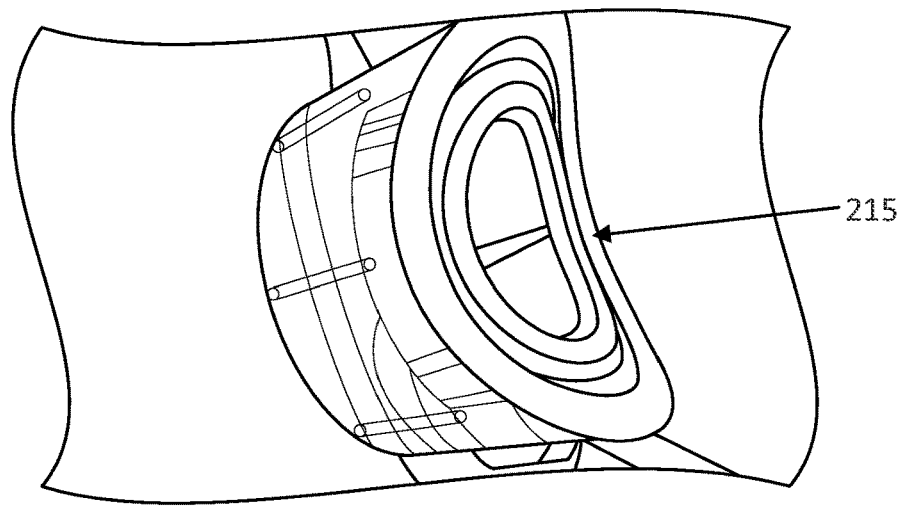

FIGS. 2A-2B are representations of two subject interface units that couple to the NO delivery device, according to an embodiment of the present disclosure. The subject interface units are the components of the gNO delivery system that are placed directly on the subject, for example, around a wound site, such that gNO is delivered to the wound site. The subject interface unit generally includes an attachment mechanism for securing the subject interface unit onto the subject and/or maintaining or creating a seal on the subject. In some aspects, as illustrated in FIG. 2A, the subject interface unit 205 is cup-shaped and includes mounting straps 210 that are light, easy to manipulate, and are made from materials suitable for attachment to a subject. In some aspects, as illustrated in FIG. 2B, the subject interface unit 215 is more rigid, and includes a peripheral vacuum unit (not illustrated) that aids in the establishment and maintenance of a seal around the gNO delivery port. Other embodiments disclosed herein relate to a subject interface unit having a strap, using a vacuum unit, negative pressure, adhesives, a gasket, a sleeve, a cup or other formed structure with a seal, or other similar device to temporarily secure the subject interface unit to the subject.

Figure 2C:
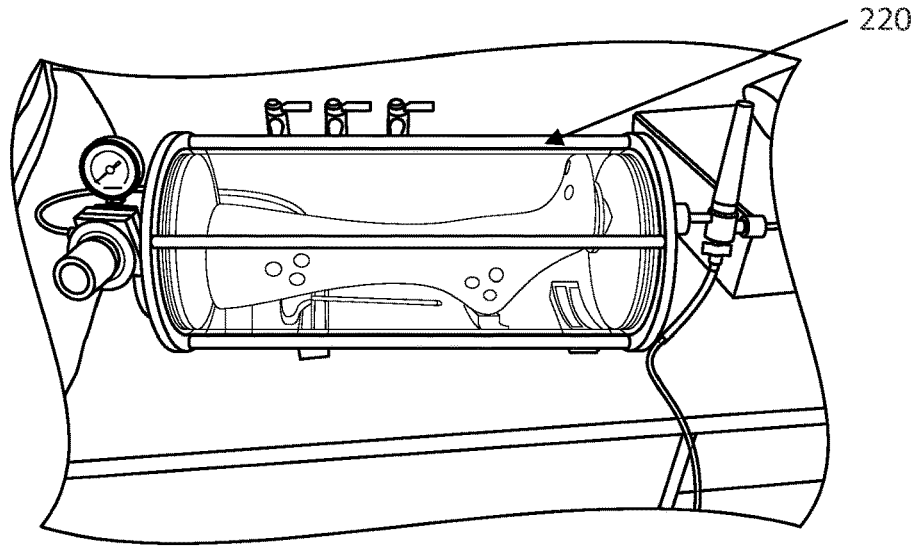

In other aspects, as illustrated in FIG. 2C, the subject interface unit 220 is configured to fit around a larger area of a subject's appendage. The subject interface unit 220 can be a flexible transparent enclosure that covers, for example, the entire foot or hand of a subject. The subject interface unit 220 can also be a rigid box-like or cylindrical structure that encloses most of the subject's leg or arm, for example, and is configured to form a seal around the more proximal region of the leg or arm. Other configurations of the subject interface unit and the attachment mechanisms can be employed in order to secure the subject interface unit on the subject and to ensure the effective deliver of gNO the subject. As would be recognized by one of ordinary skill in the art based on the present disclosure, such configurations and material used for a subject interface unit depend on factors such as, but not limited to, the size of the treatment site, its location on the subject, the type of infection, and the like.

Figure 3:
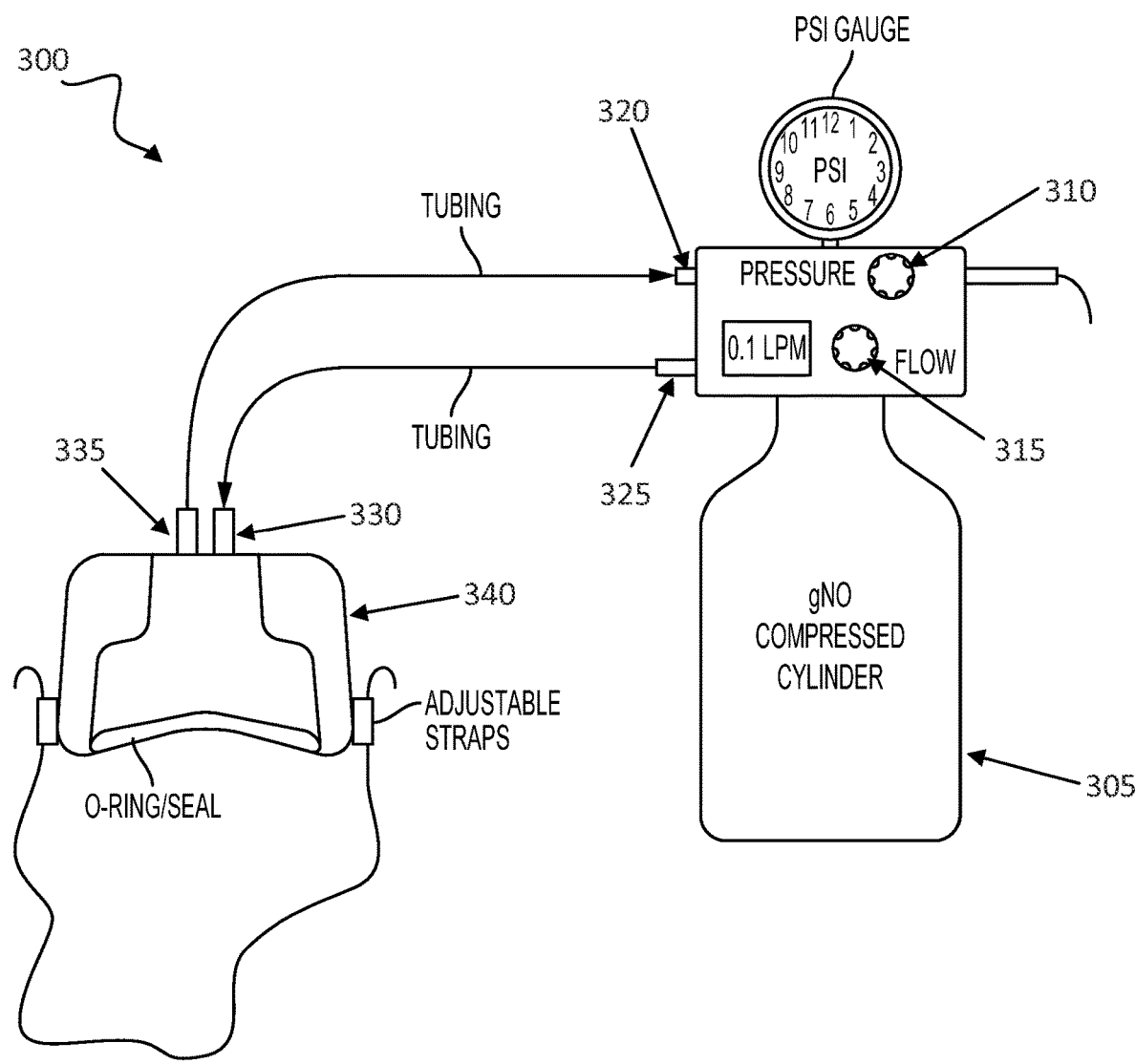
FIG. 3 is a representative drawing of a portable gNO delivery device that does not require a controller or housing, according to an embodiment of the present disclosure.
Figure 7:
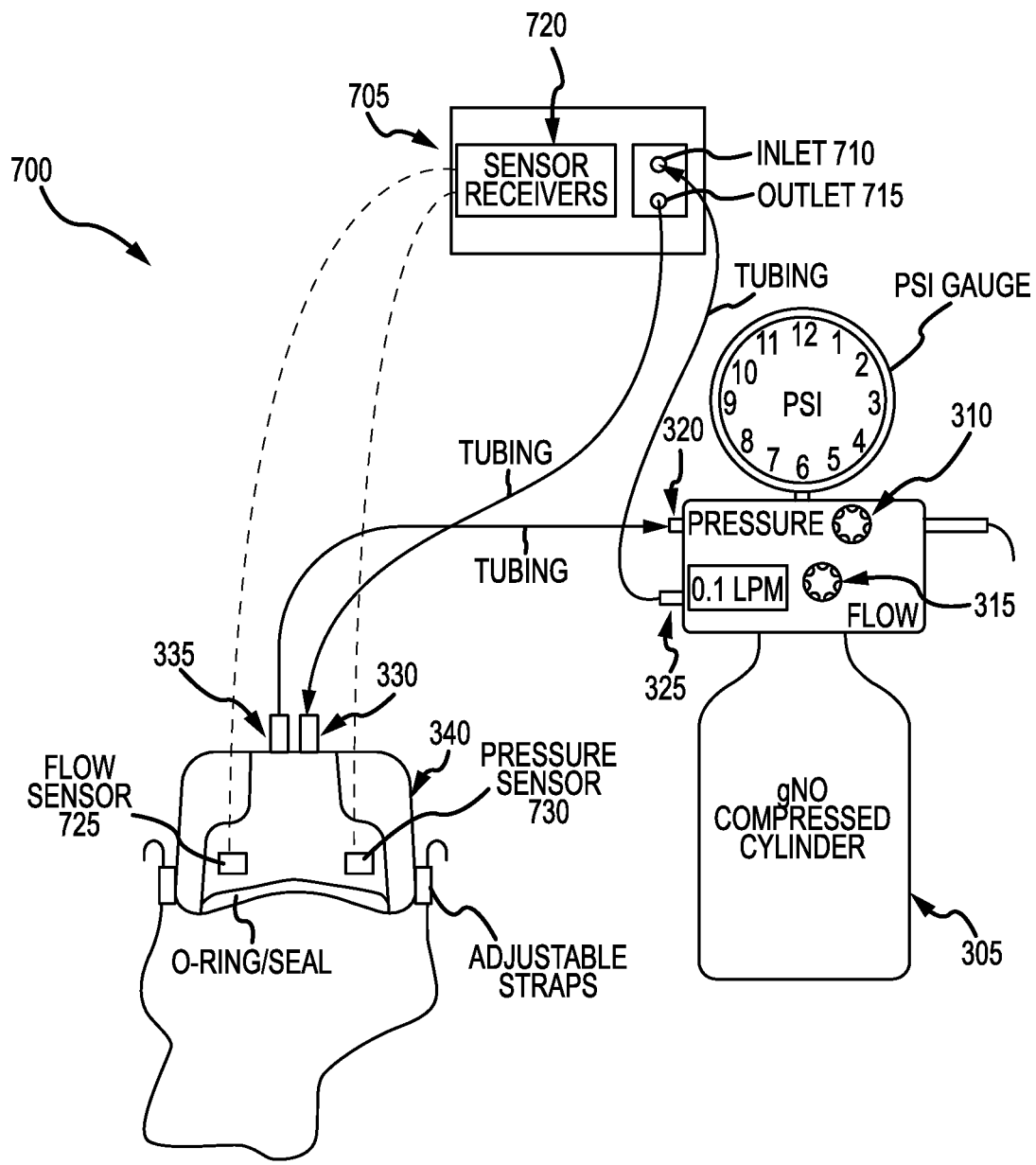
FIG. 7 is a representative illustration of a portable gNO delivery device having a manifold and feedback sensors to the manifold, according to one embodiment of the present disclosure.

In other embodiments, as illustrated in FIGS. 8A-8C, subject interface units as illustrated and contemplated herein can further include one or more sensors positioned within the subject interface unit. In some embodiments, a subject interface unit can include one or more flow sensors 805 and/or one or more pressure sensors 810. In some embodiments, the one or more flow sensors 805 and/or the one or more pressure sensors 810 can be operably connected to a manifold, housing or portable unit capable of receiving the information from the sensors. In certain embodiments, one or more of gNO flow and/or gNO pressure within a subject interface units can be remotely controlled. In certain embodiments, as illustrated in FIG. 7, a signal is received by a manifold, housing or portable unit in order to receive a signal and based on the transmitted information; adjust flow and/or gNO pressure, as necessary, to the subject interface unit. It is contemplated herein that the one or more flow sensors 805 and/or the one or more pressure sensors 810 sense the flow and/or pressure in order to feedback to a control unit for continuous or intermittent flow of gNO to the subject interface unit for a predetermined period of time and/or for a predetermined pressure to be achieved. In other embodiments, the one or more flow sensors 805 and/or the one or more pressure sensors 810 can be positioned in a subject interface unit adjacent to or in close proximity to the gNO inlet, at a median position from the gNO inlet or at the furthest position away from the gNO inlet as illustrated in FIG. 3, 330. It is contemplated that there can be more than one low sensor and/or pressure sensor strategically positioned in a subject interface unit depending on the specific subject interface unit and/or the subject's treatment site (e.g. arm, hand, foot, leg or other location). In certain embodiments, the one or more sensors located in a subject interface unit are removable as necessary to sterilize or treat a subject interface unit for reuse. In some aspect, the one or more sensors or are positionable within the subject interface unit, removable or affixed to the subject interface unit in a semi- or permanent fashion. In certain embodiments, a subject interface unit is disposable. In other embodiments, a subject interface unit is re-useable for the same or a different subject.

In some embodiments, the gNO delivery devices and systems of the present disclosure can be configured such that the gas housing unit is not required, as illustrated in FIG. 3. For example, the gNO delivery device 300 can include a source for the gNO 305 (e.g., cylinder or tank) that is directly and functionally coupled to mechanisms for regulating gNO pressure and flow to the subject interface unit, such as a gas pressure regulator 310 and/or a gas flow regulator 315. The gNO delivery device 300 can also include digital and/or analog readouts or displays for visualizing the pressure and flow of the gNO being delivered to the subject interface unit (e.g., pressure gauge, flow gauge). The gNO delivery device 300 can also include fine and/or coarse adjustment knobs for adjusting the pressure and flow of the gNO being delivered. The gNO delivery device 300 can also include gas inlets 320 and gas outlets 325 coupled to the pressure and flow regulators, as well as gas inlets 330 and gas outlets 335 coupled to the subject interface unit 340. The gNO delivery device 300 can further include tubing or other delivery component for delivering the gNO to the subject interface unit 340 and remove excess gas (e.g. to relieve pressure for example) from the subject interface unit 340. In yet other embodiments, a gNO delivery device 300 can include a feature that captures (not shown) excess gNO such as a trap or a filter unit or other comparable feature to reduce or prevent the subject from being exposed to gNO when the subject interface unit is removed.

Various embodiments of the gNO delivery device 300 can provide the added benefits of not requiring a housing unit or any electronic components; therefore, the gNO delivery device can be more easily deployed in emergency medical situations or to remote locations. In some aspects, the gNO cylinder used with these gNO devices can include a specific amount of gNO (e.g., liters of gNO), such that the delivery of the gNO to a subject constitutes a single treatment. For example, a gNO storage cylinder can contain approximately 9.0 liters of gNO such that when it is delivered to a subject for 90 continuous minutes at a flow rate of 0.1 liters per minute (LPM), the gNO will be exhausted. In other embodiments, a gNO storage cylinder can contain a predetermined amount of gNO for example, when it is delivered to a subject intermittently for a predetermined treatment time and a predetermined flow rate (e.g. 0.1 liters per minute (LPM) when delivering gas to the subject), the gNO will be exhausted. In this manner of operation, the gNO storage cylinder of gNO delivery device 300 can function as a safety feature to prevent gNO overexposure to the subject.

In some embodiments, the gNO delivery devices and systems of the present disclosure can be configured such that the gas housing unit or manifold is included, as illustrated in FIG. 7. For example, the gNO delivery device 700 can include a source for the gNO 305 (e.g., cylinder or tank) that is directly and functionally coupled to mechanisms for regulating gNO pressure and flow to the subject interface unit, such as a gas pressure regulator 310 and/or a gas flow regulator 315. The gNO delivery device 700 can also include digital and/or analog readouts or displays for visualizing the pressure and flow of the gNO being delivered to the subject interface unit (e.g., pressure gauge, flow gauge). The gNO delivery device 700 can also include fine and/or coarse adjustment knobs for adjusting the pressure and flow of the gNO being delivered. The gNO delivery device 700 can also include gas inlets 320 and gas outlets 325 coupled to the pressure and flow regulators, as well as gas inlets 330 and gas outlets 335 coupled to the subject interface unit 340. The gNO delivery device 700 can further include tubing or other delivery component for delivering the gNO to the manifold or housing unit 705 through an inlet 710. The manifold or housing unit 705 can further include an outlet 715 for delivery of the gNO to the subject interface unit 340 using a tube or other suitable delivery mechanism. The subject interface unit 340 can include an outlet 335 to remove excess gas or relieve pressure from the subject interface unit 340. In another aspect, gNO delivery device 700 can include a subject interface unit having sensors such as a flow sensor 725 and a pressure sensor 730 for sensing flow and pressure for example to feedback on the manifold or housing 705 received by a sensor receiver 720 as a relay to adjust pressure and/or gNO flow as needed. In certain embodiments, the manifold or housing 705 contains a programmable feature for regulating flow and pressure of the gNO to the subject interface unit for increased efficiency and safety of treatment. Feedback systems contemplated herein can require monitoring and adjustment by the healthcare provider in order to deliver a predetermined pressure and flow of gNO to a subject in need thereof. In certain embodiments, the manifold or housing 705 houses a controller for manual or automated adjustment of gNO flow and/or pressure, as necessary. In yet other embodiments, a gNO delivery device 700 can include a feature that captures (not shown) excess gNO such as a trap or a filter unit or other comparable feature to reduce or prevent the subject from being exposed to gNO when the subject interface unit is removed.

Various embodiments of the gNO delivery device 700 can include a manifold or feedback system as a single unit that includes a pressure and flow valve, an inlet connected to a gNO source 305 and a gas outlet 325 and capture or venting system receiver 320 attached to the subject interface unit. In some aspects, the gNO cylinder used with these gNO devices can include a specific amount of gNO (e.g., liters of gNO), such that the delivery of the gNO to a subject constitutes a single treatment. For example, a gNO storage cylinder can contain approximately 9.0 liters of gNO such that when it is delivered to a subject for 90 continuous minutes at a flow rate of 0.1 liters per minute (LPM), the gNO will be exhausted. In other embodiments, a gNO storage cylinder can contain a predetermined amount of gNO for example, when it is delivered to a subject intermittently for a predetermined treatment time and a predetermined flow rate (e.g. 0.1 liters per minute (LPM) when delivering gas to the subject), the gNO will be exhausted. In this manner of operation, the gNO storage cylinder of gNO delivery device 300 can function as a safety feature to prevent gNO overexposure to the subject.

The subject interface units and any other component of a gNO delivery device of the present disclosure can be coated with substances that help to prevent or reduce contamination from microorganisms, bacteria, fungi, viruses, and the like. The coatings can be active pharmaceutical agents that reduce the growth and/or survival of these harmful microorganisms (e.g., anti-bacterial substances), and/or the coatings can function passively to prevent or reduce contamination, for example, by preventing adherence of these microorganism to the various surfaces of the subject interface units (e.g., wetting agents). In addition, the subject interface units are readily removable for cleaning such as autoclaving or other sterilization methods for reuse on the same or a different subject. Alternatively, the subject interface units can be made of disposable material(s) for single use applications. In other embodiments, the subject interface units are made of recyclable materials.

Suitable materials that can be used to construct the subject interface units of the present disclosure include, but are not limited to, various plastics and polymers materials, such as polystyrene (PS), polycarbonate (PC), acrylonitrile-butadiene-styrene (ABS), polybutylene terephthalate (PBTP), styrene acrylonitrile (SAN), polyamide (PA), polyoxymethylene (POM), polyphenylene oxide (PPO), PE, PP, PTFE and homopolymers and copolymers of these plastics and similar materials known in the art and based on the present disclosure. The plastics may also be used in a filled or fiber-reinforced form, and/or coupled to portions of metals or metal alloys, such as aluminum, titanium, steel, and combinations thereof. The materials used to construct the subject interface units can be surface-coated, for example with paints, varnishes or lacquers. The use of color plastics, for example colored with pigments, is also possible. In other embodiments, a subject interface unit can be made of a material that is pre-molded in a customized manner to suit a particular subject or a particular location on a subject, for example, for more effective treatment. In certain embodiments, a subject can be pre-fitted or measured for a subject interface unit prior to administration of a treatment to the subject for a more effective treatment. For example, if the subject is suffering from a life-threatening infection where increased effectiveness of a single treatment is desire, the subject interface unit can include a customized fitting unit made of readily moldable materials.

Other subject interface units can be constructed, depending on the characteristics of the wound site, the location of the wound site, the condition of the subject, the environment in which the subject is to be treated, and the like. In some aspects, the various subject interface units can be adapted to model use on a subject, but applied to an in vitro setting, for experimental purposes (see, e.g., FIG. 2C). For example, a prosthetic leg or arm can be placed in a sealed, cylindrically-shaped subject interface unit configured to receive cultured cells and/or tissues (e.g., full-thickness skin tissue). Such configurations can be used to conduct experiments prior to use a live subject.

Whatever the configuration of the subject interface unit, it is beneficial to establish and maintain a seal on the subject so that gNO can be administered at sufficiently elevated pressures to provide therapeutic benefits to the subject (e.g., reducing bioburden, reduce infection, accelerate wound healing and the like). As disclosed herein, bioburden generally refers to the number of bacteria or other pathogens present on a surface or harbored within, for example, a tissue or wound (e.g., skin and/or bone). Reducing bioburden generally correlates with reducing, minimizing or eliminating an infection, as well as the various symptoms that accompany an infection (e.g., pain, swelling, redness, foul odor, blood or pus being released, etc.). Reducing bioburden and reducing infection also tend to correlate with accelerated wound healing, tissue repair, and the growth of healthy tissue. The application of pressurized gNO for a given amount of time at a given flow rate can reduce bioburden in the wound of a subject, which in turn promotes healing.

The gNO delivery systems of the present disclosure can include subject interface units having the ability to maintain a seal on a subject when administering gNO at about 0.1 ATM (1.47 psi) to about 1.0 ATM (14.695 psi). In some aspects, administering gNO at a pressure ranging from about 0.1 ATM (1.47 psi) to about 0.25 ATM (3.674 psi) is capable of establishing and maintaining a seal of the subject interface unit to the wound site or surrounding wound area or infected area of a subject and reduce bioburden in the wound, thereby accelerating healing and reducing spread of targeted microorganisms. In other aspects, administering gNO at a pressure ranging from about 0.1 ATM (1.47 psi) to about 0.15 ATM (2.20 psi) is capable of establishing and maintaining a seal of the subject interface unit to the wound site or surrounding wound area or infected area of a subject and to reduce bioburden in the wound, thereby accelerating healing and reducing spread of targeted microorganisms. Administering gNO in these pressure ranges is sufficient to reduce bioburden without significantly compromising the viability of the cells and tissues of the subject.

In some embodiments, the gNO delivery systems of the present disclosure can be used to administer gNO to the site of a subject's wound at a certain flow rate. As would be recognized by one of ordinary skill in the art and based on the present disclosure, units of flow rate can be expressed using various metrics, including liters/minute (LPM) and/or cubic centimeters per minute ($cm^3$/min or cc/min). For example, gNO can be delivered to a subject at a flow rate ranging from about 0.1 liters/minute to about 2.0 liters/ minute, from about 0.1 liters/minute to about 1.9 liters/minute, from about 0.1 liters/minute to about 1.8 liters/minute, from about 0.1 liters/minute to about 1.7 liters/minute, from about 0.1 liters/minute to about 1.6 liters/minute, from about 0.1 liters/minute to about 1.5 liters/minute, from about 0.1 liters/minute to about 1.4 liters/minute, from about 0.1 liters/minute to about 1.3 liters/minute, from about 0.1 liters/minute to about 1.2 liters/minute, from about 0.1 to about 1.1 liters/minute, from about 0.1 liters/minute to about 1.0 liters/minute, from about 0.1 liters/minute to about 0.9 liters/minute, from about 0.1 liters/minute to about 0.8 liters/minute, from about 0.1 liters/minute to about 0.7 liters/minute, from about 0.1 liters/minute to about 0.6 liters/minute, from about 0.1 liters/minute to about 0.5 liters/minute, from about 0.1 liters/minute to about 0.4 liters/minute, from about 0.1 liters/minute to about 0.3 liters/minute, and from about 0.1 liters/minute to about 0.2 liters/minute. In some aspects, the NO can be delivered to a subject at a flow rate of about 0.1 liters/minute, about 0.2 liters/minute, about 0.3 liters/minute, about 0.4 liters/minute, about 0.5 liters/minute, about 0.6 liters/minute, about 0.7 liters/minute, about 0.8 liters/minute, and about 0.9 liters/minute, about 1.0 liters/minute, about 1.2 liters/minute, about 1.3 liters/minute, about 1.4 liters/minute, about 1.5 liters/minute, about 1.6 liters/minute, about 1.7 liters/minute, about 1.8 liters/minute, about 1.9 liters/minute, and about 2.0 liters/minute, or equivalent.

In some embodiments, the gNO delivery systems of the present disclosure can be used to administer gNO to the site of a subject's wound for a certain period or predetermined period of time either continuously or intermittently. For example, gNO can be delivered to a subject for a period of time ranging from about 30 minutes to about 180 minutes, from about 30 minutes to about 170 minutes, from about 30 minutes to about 160 minutes, from about 30 minutes to about 150 minutes, from about 30 minutes to about 140 minutes, from about 30 minutes to about 130 minutes, from about 30 minutes to about 120 minutes, from about 30 minutes to about 110 minutes, from about 30 minutes to about 90 minutes, from about 30 minutes to about 80 minutes, from about 30 minutes to about 70 minutes, from about 30 minutes to about 60 minutes, from about 30 minutes to about 50 minutes, and from about 30 minutes to about 40 minutes either continuously or intermittently. In some aspects, gNO can be delivered to a subject for a period of time either continuously or intermittently of about 110 minutes, about 105 minutes, about 100 minutes, about 95 minutes, about 90 minutes, about 85 minutes, about 80 minutes, about 75 minutes, about 70 minutes, about 65 minutes, about 60 minutes, about 55 minutes, about 50 minutes, about 45 minutes, about 40 minutes, about 35 minutes, about 30 minutes, about 25 minutes, about 20 minutes, about 15 minutes, about 10 minutes, and about 5 minutes, or as determined to be appropriate for the subject and wound or area under examination or to be treated.

In some embodiments, gNO delivery devices and systems of the present disclosure can include one or more gas sensors (e.g., electrochemical sensors) for measuring the concentration of one or more gases being delivered to the subject (FIG. 1, 135). For example, the delivery systems of the present disclosure can include nitric oxide sensors, nitric dioxide sensors, and/or oxygen sensors. These sensors can be functionally coupled to the source of the gas (e.g., gNO tank or cylinder) and/or they can be coupled to the subject interface unit to measure gas concentrations, gas pressures or gas flow at the site of the wound or infection. In some aspects, gas sensors can be of use to maintain a constant flow rate and concentration of gNO over a given treatment period or of use to maintain a predetermined intermitted delivery of gNO over a given treatment period. In some aspects, the sensors can indicate to a user (e.g., health care provider) that the concentration of the gas is above or below a prescribed threshold for a given treatment protocol for a subject, in which case the user can adjust one or more parameters, such as the gas pressure regulator or the gas flow regulator, or the user can stop the treatment and replace the source of the gas with one having the appropriate concentrations of gases. In some embodiments, the sensors can be used to feedback to a manifold or other housing where the concentration of the gas is above or below a prescribed threshold for a given treatment protocol for a subject, in which case the system has the ability to automatically adjust one or more parameters, such as the gas pressure or the gas flow to the subject in order to deliver an appropriate pressure and flow of the gNO to the subject. In other aspects, the gas sensors can be used as part of a protocol to purge the system, including the subject interface unit, of oxygen, such that gNO can be delivered to a subject in a manner that is substantially free of oxygen, such as, for increased efficacy of the gNO treatment. For example, a continuous stream of gNO and/or a bolus of gNO can be delivered to a subject through the subject interface unit while an oxygen sensor measures the decreasing concentration of oxygen in the subject interface unit. Once the sensor indicates that little to no oxygen is present in the system, the gNO treatment protocol can commence.

Additionally, the gNO delivery devices and systems of the present disclosure can include a flushing mechanism. In some aspects, the flushing mechanism can be used to flush out the NO used during treatment and restore oxygen levels to normal or a control level so that the subject is not exposed to elevated levels of NO after the subject interface unit is removed. The flushing mechanism can be coupled to the gNO gas controller or housing, such that a user can replace or switch the source of the gNO used for treatment with a source of gas having a lower concentration of gNO and a higher concentration of oxygen (e.g., cylinder having compressed ambient air or pure oxygen). In some aspects, the user can activate the flushing mechanism to displace the previously administered gNO out of the subject interface unit. The flushing mechanism can be performed according to a prescribed protocol, for example, the flushing gas can be administered over a certain duration of time while the subject interface unit is still attached to the subject. In some aspects, the flushing mechanism can include the injection of a bolus of air or purified oxygen into the delivery device soon after the gNO treatment has ended. In this manner of operation, there is no significant need for a flushing protocol, as the bolus of air will be injected and travel through the delivery device rapidly. Other flushing protocols can be used according to accepted medical standards and practices, as would be recognized by one of ordinary skill in the art based on the present disclosure.

Embodiments of the gNO delivery systems of the present disclosure can be used to alleviate disease symptoms or health conditions and improve therapeutic outcomes in a subject regarding wounds. For example, the gNO delivery systems of the present disclosure can be used to treat subjects having health conditions, for example, diabetes mellitus, as these subjects are known to be at risk for developing acute as well as chronic dermal ulcers (e.g., foot ulcers), for example due to established long-term complications of the health condition or disease. Infections due to diabetic ulcers can range in severity from superficial paronychia to deep infections involving bone. It is contemplated herein that any and all of these types of ulcers can be treated using systems and methods of the present disclosure. In certain embodiments, types of infection that can be treated by gNO delivery systems of embodiments herein can include, but are not limited to, cellulitis, myositis, abscesses, necrotizing fasciitis, septic arthritis, tendinitis, and osteomyelitis.

In some embodiments, gNO delivery systems of the present disclosure can be used to treat skin and soft tissue infections (SSTIs). SSTIs are common, and complicated SSTIs (cSSTIs) can be a more severe form of this indication. SSTIs can encompass a range of clinical presentations, including but not limited to, deep-seated infection, which typically requires surgical intervention, the presence of systemic signs of sepsis, the presence of complicating co-morbidities, accompanying neutropenia, accompanying ischemia, accompanying tissue necrosis, burns as well as insect bites. Staphylococcus aureus is the most common cause of SSTI; however, its epidemiology (e.g., causative strains) and antibiotic susceptibility are often unpredictable. It is contemplated that systems and methods disclosed herein can be used to reduce the risk of developing SSTIs as well as treating them.

Various embodiments of the gNO delivery systems disclosed in the present application can provide the means to minimize infection by reducing bioburden using pressurized gNO delivered to a wound site. Unlike antibiotic-related treatments against pathogenic organisms such as bacteria, bacteria are incapable of developing resistance to gNO. Therefore, gNO delivery systems of the present disclosure represent a universally effective means to treat and/or prevent infections by reducing bioburden in a wound or infection site and reduce bioburden and accelerate healing. Other embodiments of the present application include gNO delivery systems for use in reducing infections already present in a subject, and/or for use to prophylactically treat onset or development of a pathogenic infection, for example, by being applied to the site of a surgical wound or incision. Additionally, gNO delivered using the systems and devices of the present disclosure can be used to treat infection in a wide range of wounds and disease indications in a subject, including, but not limited to, sites of pathogen infections such as bacterial infections, fungal infections, viral infections, protozoan infections, as well as burns, wounds, wrinkles, lesions, and the like. Lesions can include, but are not limited to, a surgical wound or site, a trauma-related wound, a burn, an abscess, an actinic keratosis, a keloid, a scar, skin cancer sites and a combination thereof.

In other embodiments of the present disclosure, gNO delivery systems can be used in combination with other therapies to alleviate disease symptoms and improve therapeutic outcomes in a subject in need of such a treatment. For example, in the case of osteomyelitis, gNO administration according to embodiments of the present disclosure can be combined with other known treatment methods, including but not limited to, antibiotic administration, hyperbaric oxygen therapy (HBO), maggot debridement therapy, and granulocyte colony-stimulating factor administration. In some aspects, combinatorial therapy can have synergistic effects and can preclude the need for surgical intervention, such as amputation.

EXAMPLES

Figure 4:
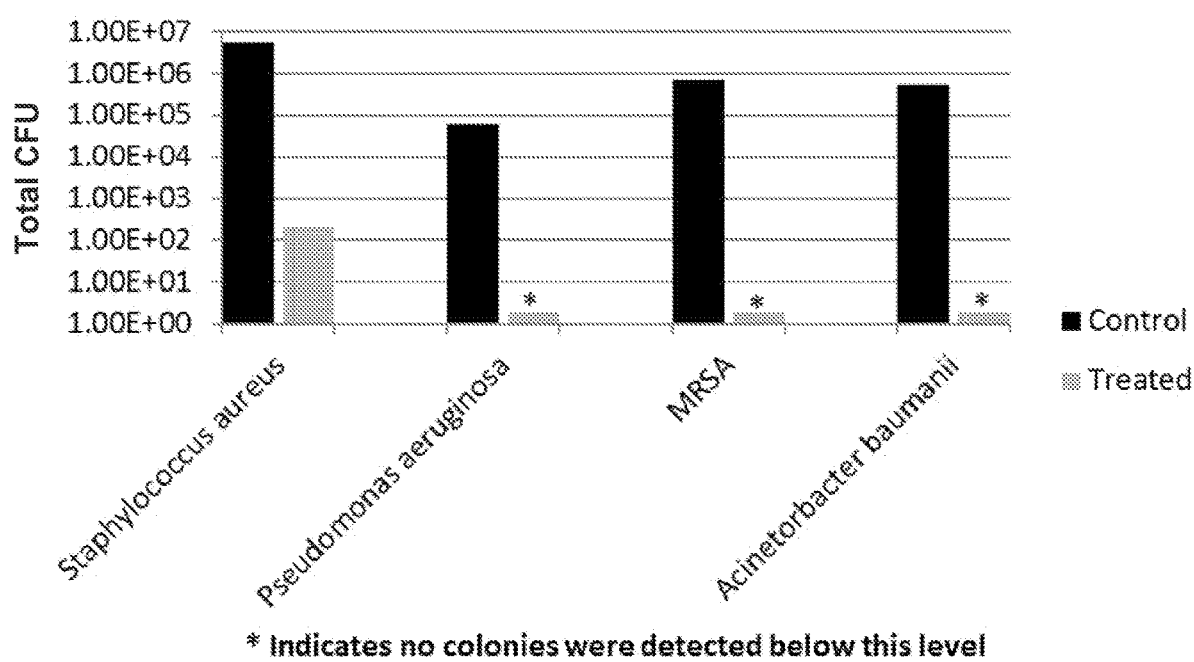
FIG. 4 is a graph illustrating the effects of gNO treatment on bioburden after three hours of bacterial infection, according to an embodiment of the present disclosure.

Examples of the present disclosure are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein. Reduction in bioburden FIG. 4 is a graph illustrating the effects of NO treatment on bioburden using an infection assay, after three hours of infection, according to an embodiment of the present disclosure. Skin samples infected for 3 hours with Staphylococcus, MRSA, Acinetobacter or Pseudomonas and subsequently exposed to 1% gNO at 1 ATM (14.695 psi) for 90 minutes at a flow rate of 0.1 liters/minute. Staphylococcus aureus, subspecies aureus Rosenbach (ATCC #12600); Staphylococcus aureus, subspecies aureus Rosenbach (ATCC #33591), methicillin-resistant strain of Staphylococcus aureus, phage type 92; Acinetobacter baumannii (ATCC #BAA-747); and Pseudomonas aeruginosa (ATTC #BAA-47). Control=infected, untreated tissue. Three sets of triplicates were performed per experiment.

As illustrated in FIG. 4, treatment that included 1% gNO at 1 ATM (14.695 psi) for 90 minutes significantly reduced bioburden in each of the four types of bacteria tested. S. aureus was reduced 5-fold, and the other bacterial strains were nearly completely eradicated. These results demonstrate the efficacy of gNO administration for reducing infection by reducing bioburden in the wound of a subject. Additionally, because these experiments were performed using an acute 3 hour infection model, these data also indicate that gNO treatment according to the above therapeutic parameters can be used to reduce onset as well as prevent infections as well as to treat infections.

Reduction in Bioburden at Pressures Below 1.0 ATM

Experiments were also conducted to determine the infection-reducing capability of gNO administration at various pressures below 1.0 ATM (14.695 psi) (independent of and in addition to the pressure applied by the external environment) using both a Franz cell tissue culture device (i.e., 3-Ring) and a portable gNO deliver device (i.e., Leg Device). The results of one set of experiments are illustrated below in Table 1. gNO was administered at a 1% concentration after 24 hours of infection with S. aureus. Flow Rates ($cm^3$/min or cc) varied from about 100 to about 1500, Purge Flow (liters/min or LPM) varied from about 0.1 to about 1.5, and gNO Exposure Time varied between about 45 minutes to about 105 minutes among the different treatment groups and controls. Colony counts (log CFU) were performed at various dilutions, which are represented in the last eight columns labeled 0, $1 \times 10^{-1}$ through $1 \times 10^{-7}$ ("0" indicates no dilution). The results in Table 1 demonstrate that bioburden was significantly reduced (i.e., total kill) after gNO administration at pressures as low as about 0.15 ATM (2.2 psi) for exposure times of about 105 minutes.

Additionally, MTT assays were performed to assess cell viability after gNO administration. MTT assays are colorimetric-based assays used to assess cell viability as a function of color variation. As illustrated below in Table 2, cell viability after the administration of pressurized gNO at about 0.15 ATM (2.2 psi) for about 105 minutes varied from about 40%-50%. Therefore, the administration of gNO at pressures less than 1.0 ATM (14.695 psi) is effective for reducing bioburden and does not significantly compromise cell viability.

The results in Tables 2 and 3 indicate that gNO can be delivered at pressures below 1.0 ATM (14.695 psi) (independent of and in addition to the pressure applied by the external environment) and effectively reduce infection by reducing bioburden without significantly compromising the viability of the subject's cells. The use of pressures below 1.0 ATM (14.695 psi) have the additional benefit of requiring less external pressure on the subject interface unit to maintain a seal, thus making the seal easier to establish and maintain, as well as providing a greater degree of comfort for the subject. Striking the balance between delivering gNO at a high enough pressure to penetrate the skin and reduce bioburden and yet still maintain an effective seal on the subject is one important contribution of the present disclosure.

TABLE 1

The effect of pressurized gNO administration on reducing bioburden

| Trial | Sample | Franz cell Version | Purge Flow (LPM) | Flow rate (cc) | Pressure Delivered (ATM) | Exposure Time (min) | 0 | 1 × 10-1 |
|---|---|---|---|---|---|---|---|---|
| Control | | | | | | | TNTC | TNTC |
| Leg 1 | A | Leg Device | 1.5 LPM | 1500 | 1 ATM | 90 min | 0 | 0 |
| Leg 1 | B | Leg Device | 1.5 LPM | 1500 | 1 ATM | 90 min | 0 | 0 |
| Leg 1 | C | Leg Device | 1.5 LPM | 1500 | 1 ATM | 90 min | 0 | 0 |
| 0.5 ATM | A | 3-Ring | 0.1 | 100 | 0.5 ATM | 90 min | 0 | 0 |
| 0.5 ATM | B | 3-Ring | 0.1 | 100 | 0.5 ATM | 90 min | 16 | 2 |
| 0.5 ATM | C | 3-Ring | 0.1 | 100 | 0.5 ATM | 90 min | 0 | 0 |
| Control | | | | | | | TNTC | TNTC |
| Leg 2 | A | Leg Device | 1.5 LPM | 100 | 0.5 ATM | 90 min | 0 | 0 |
| Leg 2 | B | Leg Device | 1.5 LPM | 100 | 0.5 ATM | 90 min | 0 | 0 |
| Leg 2 | C | Leg Device | 1.5 LPM | 100 | 0.5 ATM | 90 min | 0 | 0 |
| Control | | | | | | | TNTC | TNTC |
| Calf | A | Leg Device | 0.1 | 100 | 0.5 ATM | 90 min | 0 | 0 |
| Heel | B | Leg Device | 0.1 | 100 | 0.5 ATM | 90 min | 0 | 0 |
| Toe | C | Leg Device | 0.1 | 100 | 0.5 ATM | 90 min | 0 | 0 |
| 0.25 ATM | A | 3-Ring | 0.1 | 100 | 0.25 ATM | 90 min | 0 | 0 |
| 0.25 ATM | B | 3-Ring | 0.1 | 100 | 0.25 ATM | 90 min | 0 | 0 |
| 0.25 ATM | C | 3-Ring | 0.1 | 100 | 0.25 ATM | 90 min | 0 | 0 |
| Control | | | | | | | TNTC | TNTC |
| 0.5 ATM | A | Leg Device | 1.0 LPM | 500 | 0.5 ATM | 45 min | 0 | 0 |
| 0.5 ATM | B | Leg Device | 1.0 LPM | 500 | 0.5 ATM | 45 min | 0 | 0 |
| 0.5 ATM | C | Leg Device | 1.0 LPM | 500 | 0.5 ATM | 45 min | 0 | 0 |
| Control | | | | | | | TNTC | TNTC |
| d Pressure | A | Leg Device | 0.1 | 100 | 0.5 ATM | 45 min | TNTC | TNTC |
| d Pressure | B | Leg Device | 0.1 | 100 | 0.5 ATM | 45 min | TNTC | TNTC |
| d Pressure | C | Leg Device | 0.1 | 100 | 0.5 ATM | 45 min | TNTC | TNTC |
| Control | | | | | | | TNTC | TNTC |
| 0.25 ATM | A | 3-Ring | 0.1 | 100 | 0.25 ATM | 90 min | 0 | 0 |
| 0.25 ATM | B | 3-Ring | 0.1 | 100 | 0.25 ATM | 90 min | 0 | 0 |
| 0.25 ATM | C | 3-Ring | 0.1 | 100 | 0.25 ATM | 90 min | 0 | 0 |
| 0.25 ATM | A | 3-Ring | 0.1 | 100 | 0.25 ATM | 90 min | TNTC | TNTC |
| 0.25 ATM | B | 3-Ring | 0.1 | 100 | 0.25 ATM | 90 min | TNTC | TNTC |
| 0.25 ATM | C | 3-Ring | 0.1 | 100 | 0.25 ATM | 90 min | TNTC | TNTC |
| Control | | | | | | | TNTC | TNTC |
| 9 attempt | A | 3-Ring | 0.1 | 100 | 0.25 ATM | 90 min | TNTC | TNTC |
| 9 attempt | B | 3-Ring | 0.1 | 100 | 0.25 ATM | 90 min | TNTC | TNTC |
| 9 attempt | C | 3-Ring | 0.1 | 100 | 0.25 ATM | 90 min | TNTC | TNTC |
| Leg purge | A | Leg Device | 0.5 LPM | 100 | 0.25 ATM | 90 min | 0 | 0 |
| Leg purge | B | Leg Device | 0.5 LPM | 100 | 0.25 ATM | 90 min | 0 | 0 |
| Leg purge | C | Leg Device | 0.5 LPM | 100 | 0.25 ATM | 90 min | 0 | 0 |
| Control | | | | | | | TNTC | TNTC |
| 0.15 ATM | A | 3-Ring | 0.1 | 100 | 0.15 ATM | 105 min | TNTC | TNTC |
| 0.15 ATM | B | 3-Ring | 0.1 | 100 | 0.15 ATM | 105 min | 0 | 0 |
| 0.15 ATM | C | 3-Ring | 0.1 | 100 | 0.15 ATM | 105 min | 0 | 0 |
| Control | | | | | | | TNTC | TNTC |
| 0.15 ATM | A | 3-Ring | 0.1 | 100 | 0.15 ATM | 105 min | 0 | 0 |
| 0.15 ATM | B | 3-Ring | 0.1 | 100 | 0.15 ATM | 105 min | TNTC | TNTC |
| 0.15 ATM | C | 3-Ring | 0.1 | 100 | 0.15 ATM | 105 min | 5* | 0 |

| Trial | 1 × 10-2 | 1 × 10-3 | 1 × 10-4 | 1 × 10-5 | 1 × 10-6 | 1 × 10-7 |
|---|---|---|---|---|---|---|
| Control | TNTC | TNTC | TNTC | >250 | 47 | 3 |
| Leg 1 | 0 | 0 | 0 | 0 | 0 | 0 |
| Leg 1 | 0 | 0 | 0 | 0 | 0 | 0 |
| Leg 1 | 0 | 0 | 0 | 0 | 0 | 0 |
| 0.5 ATM | 0 | 0 | 0 | 0 | 0 | 0 |
| 0.5 ATM | 0 | 0 | 0 | 0 | 0 | 0 |
| 0.5 ATM | 0 | 0 | 0 | 0 | 0 | 0 |
| Control | TNTC | TNTC | TNTC | >250 | 46 | 3 |
| Leg 2 | 0 | 0 | 0 | 0 | 0 | 0 |
| Leg 2 | 0 | 0 | 0 | 0 | 0 | 0 |
| Leg 2 | 0 | 0 | 0 | 0 | 0 | 0 |
| Control | TNTC | TNTC | TNTC | >250 | 56 | 5 |
| Calf | 0 | 0 | 0 | 0 | 0 | 0 |
| Heel | 0 | 0 | 0 | 0 | 0 | 0 |

TABLE 1-continued

The effect of pressurized gNO administration on reducing bioburden

| | | | | | | |
|---|---|---|---|---|---|---|
| Toe | 0 | 0 | 0 | 0 | 0 | 0 |
| 0.25 ATM | 0 | 0 | 0 | 0 | 0 | 0 |
| 0.25 ATM | 0 | 0 | 0 | 0 | 0 | 0 |
| 0.25 ATM | 0 | 0 | 5 | 0 | 0 | 0 |
| Control | TNTC | TNTC | TNTC | 180 | 16 | 0 |
| 0.5 ATM | 0 | 0 | 0 | 0 | 0 | 0 |
| 0.5 ATM | 0 | 0 | 0 | 0 | 0 | 0 |
| 0.5 ATM | 0 | 0 | 0 | 0 | 0 | 0 |
| Control | TNTC | TNTC | TNTC | 67 | 4 | 0 |
| d Pressure | TNTC | TNTC | 28 | | | |
| d Pressure | TNTC | TNTC | 14 | | | |
| d Pressure | TNTC | TNTC | 40 | | | |
| Control | TNTC | TNTC | TNTC | TNTC | 59 | 6 |
| 0.25 ATM | 0 | 0 | 0 | 0 | 0 | 0 |
| 0.25 ATM | 0 | 0 | 0 | 0 | 0 | 0 |
| 0.25 ATM | 0 | 0 | 0 | 0 | 0 | 0 |
| 0.25 ATM | TNTC | TNTC | >150 | | | |
| 0.25 ATM | TNTC | TNTC | 66 | | | |
| 0.25 ATM | TNTC | TNTC | 59 | | | |
| Control | TNTC | TNTC | TNTC | TNTC | 54 | 11 |
| 9 attempt | TNTC | TNTC | 97 | | | |
| 9 attempt | TNTC | 38 | 0 | | | |
| 9 attempt | TNTC | TNTC | 188 | | | |
| Leg purge | 0 | 0 | 0 | | | |
| Leg purge | 0 | 0 | 0 | | | |
| Leg purge | 0 | 0 | 0 | | | |
| Control | TNTC | TNTC | TNTC | TNTC | 142 | 14 |
| 0.15 ATM | 181* | 20* | 1 | 0 | 0 | 0 |
| 0.15 ATM | 0 | 0 | 0 | 0 | 0 | 0 |
| 0.15 ATM | 0 | 0 | 0 | 0 | 0 | 0 |
| Control | TNTC | TNTC | TNTC | TNTC | 124 | 14 |
| 0.15 ATM | 0 | 0 | 0 | 0 | 0 | 0 |
| 0.15 ATM | 24 | 3 | 0 | 0 | 0 | 0 |
| 0.15 ATM | 0 | 0 | 0 | 0 | 0 | 0 |

TABLE 2

The effect of pressurized gNO administration on cell viability

| | OD1 | OD2 | OD3 | AVG | % Viability |
|---|---|---|---|---|---|
| Control | 1.17 | 1.219 | 1.217 | 1.202 | 100 |
| A | 0.55 | 0.532 | 0.531 | 0.538 | 44.7 |
| B | 0.554 | 0.524 | 0.517 | 0.532 | 44.2 |
| C | 0.484 | 0.48 | 0.473 | 0.479 | 39.9 |

Detection of S. aureus in Skin Infections

Figure 5A:
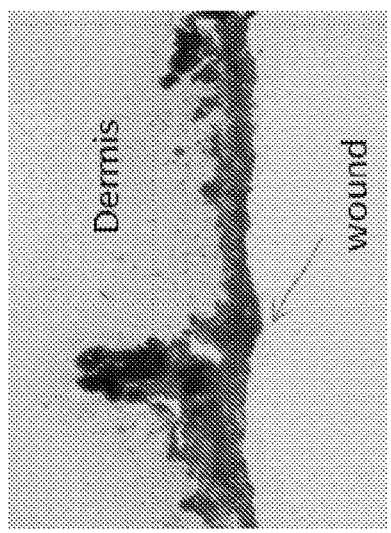
FIGS. 5A-5C are representative histological sections stained to detect the presence of bacteria on treated and untreated tissue, according to embodiments of the present disclosure.
Figure 5B:
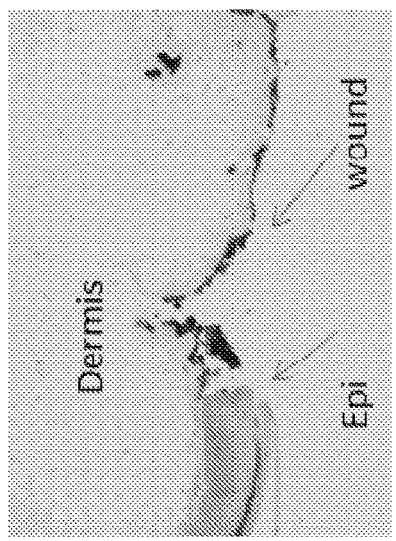
Figure 5C:
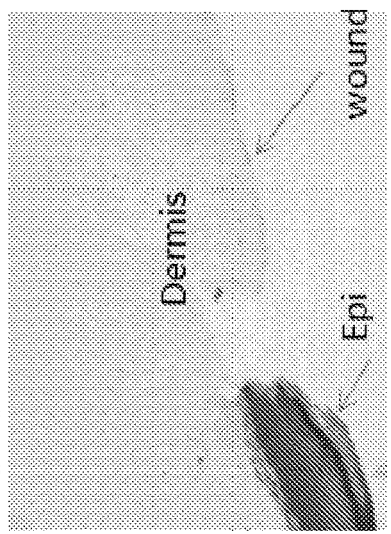

FIGS. 5A-5C are representative histological sections stained to detect the presence of S. aureus on treated and untreated skin sample tissue, according to an embodiment of the present disclosure. FIG. 5A represents an image of tissue that was wounded but left uninfected. FIG. 5B represents an image of tissue that was wounded and infected for 3 hours with S. aureus. FIG. 5C represents an image of tissue that was wounded and infected for 24 hours with S. aureus. The representative histological sections were stained with Giesma, which identifies S. aureus present in the skin sample tissue. S. aureus could be seen on the on the surface of the wound after 3 hours of infection, but by 24 hours of exposure, the bacteria had penetrated further into the tissue.
Detection of biofilm production by of S. aureus in skin infections Biofilms can play a role in histopathology and are complex structures that include bacterial cells embedded in extracellular matrices that contain for example, polysaccharides, proteins and DNA. The biofilm matrix can limit and interfere with the effect of topical antibiotic treatment in infected wounds and can impede wound healing and immune responses. The various components of biofilm and its associated extracellular matrix can be visualized using histological techniques, and can provide a basis for assessing the efficacy of gNO administration for reducing bioburden for microorganisms such as bacteria that form biofilms.

Figures 6A, 6B, 6C, 6D, 6E, 6F:
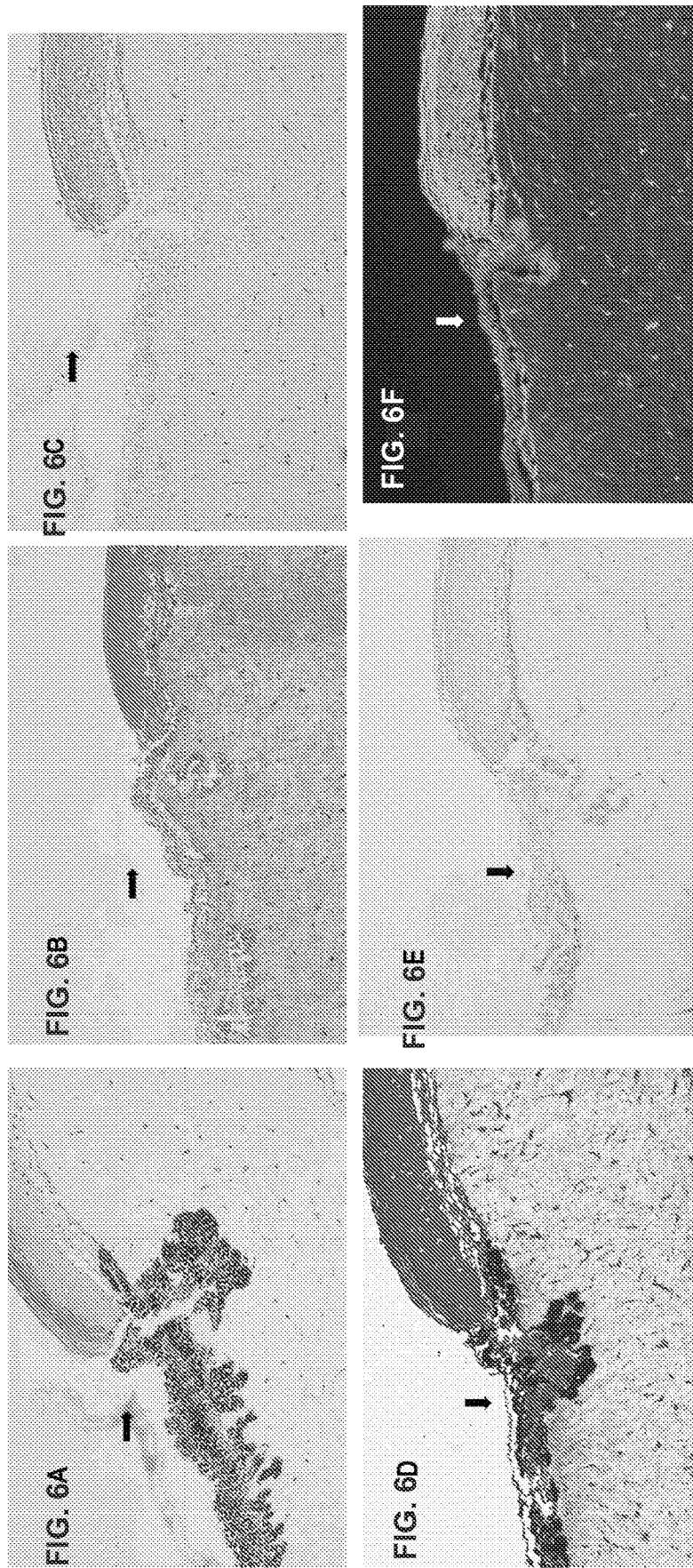
FIGS. 6A-6F are representative histological sections stained to detect components of bacterial biofilm, according to an embodiment of the present disclosure.

FIGS. 6A-6F are representative histological sections stained to detect components of bacterial biofilm, according to an embodiment of the present disclosure. The skin samples illustrated in FIGS. 6A-6F were infected for 24 hours with S. aureus bacteria, then fixed in formaline, embedded, and sliced at 5-6 μm increments. FIG. 6A represents and image of tissue stained with Hematoxylin and cosin. FIG. 6B represents an image of tissue stained with Feulgen reaction. FIG. 6C represents an image of tissue stained with Modified Congo Red. FIG. 6D represents an image of tissue stained with Modified Congo Red with Carbol Fuchsin. FIG. 6F represents an image of tissue stained with PAS. FIG. 6F represents an image of tissue stained with Calcofluor. Using these histological techniques, skin tissue sample were obtained before and after treatment with pressurized gNO to determine reductions in bioburden for bacteria that form biofilm and the effect of pressurized gNO on the components of biofilms.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A gaseous nitric oxide (gNO) delivery device for delivering pressurized gNO to a subject, the device comprising:
    a subject interface unit functionally coupled to a source of gNO;
    one or more sensors positioned within the subject interface unit, wherein the sensors comprise one or more flow sensor(s), wherein the one or more flow sensor(s) detect flow of the gNO as the gNO is delivered through the subject interface unit to the subject and relay a detected flow value to a receiver and wherein the one or more sensors ae operably connected to a manifold; and the manifold housing the receiver capable of receiving a signal from the one or more sensors.

2. The device of claim 1, further comprising one or more pressure sensor(s) positioned within the subject interface unit wherein the one or more pressure sensor(s) detect pressure of the gNO as the gNO is delivered through the subject interface unit to the subject and relay a detected pressure value to the receiver.

3. The device of claim 2, further comprising a controller for regulating at least one of the one or more sensors positioned within the subject interface unit wherein the controller is a manual controller or an automated controller for adjusting at least one of gNO flow or gNO pressure to the subject interface unit.

4. The device of claim 1, further comprising a gNO inlet in the subject interface unit and wherein the one or more sensors are located immediately adjacent to the subject interface unit gNO inlet.

5. The device of claim 1, further comprising a gNO inlet in the subject interface unit and wherein the one or more sensors are located in close proximity to the subject interface unit gNO inlet.

6. The device of claim 1, wherein pressure of the gNO delivered to the subject interface unit is about 0.15 ATM to about 1.0 ATM above ambient ATM.

7. The device of claim 1, wherein the gNO is delivered to the subject interface unit at a flow rate from about 0.1 liters/minute to about 1.0 liters/minute.

8. The device of claim 1, wherein concentration of the gNO delivered to the subject interface unit is about 1.0% to about 2%.

9. The device of claim 1, wherein the gNO is delivered to the subject interface unit continuously for a predetermined amount of time.

10. The device of claim 1, wherein the gNO is delivered to the subject interface unit intermittently for a predetermined amount of time.

11. The device of claim 1, wherein the subject interface unit further comprises a gas outlet to regulate flow of the gNO to the subject.

12. The device of claim 1, further comprising a controller for regulating at least one of the one or more sensors positioned within the subject interface unit.

13. The device of claim 1, wherein the gNO comprises a single source of therapeutic gaseous material consisting essentially of a gNO cylinder, the gNO cylinder containing a single treatment volume of gNO.

14. The device of claim 1, wherein the subject interface unit comprises an attachment mechanism for maintaining a seal on the subject while the gNO is being delivered to the subject interface unit.

15. The device of claim 14, wherein the attachment mechanism comprises one or more strap(s), vacuum, negative pressure, adhesive, gasket, O-ring, sleeve, cup or other formed structure for attaching the subject interface unit to the subject.

16. The device of claim 1, further comprising a gas flushing or gas capturing mechanism to reduce exposure of the subject to gNO when the subject interface unit is removed.

17. A method for treating a wound on a subject, the method comprising: treating the wound of the subject using the gaseous nitric oxide (gNO) delivery device of claim 1.

18. The method of claim 17, wherein the gNO is delivered to the subject interface unit intermittently for about 15 minutes to about 120 minutes.

19. The method of claim 17, wherein treating the wound comprises reducing bioburden in the wound.

20. A kit comprising: a subject interface unit for coupling to a gaseous nitric oxide (gNO) delivery device having at least one flow sensor and at least one pressure sensor positioned within the subject interface unit, wherein the at least one flow sensor detects flow of the gNO as the gNO is delivered through the subject interface unit to the subject.

21. The kit of claim 20, wherein the subject interface unit is reusable.

22. The kit of claim 20, wherein the subject interface unit is disposable.

* * * * *

UNITED STATES PATENT AND TRADEMARK OFFICE
CERTIFICATE OF CORRECTION

| | |
|---|---|
| PATENT NO. | : 11,633,551 B2 |
| APPLICATION NO. | : 16/773676 |
| DATED | : April 25, 2023 |
| INVENTOR(S) | : Jeffrey L. Jensen et al. |

It is certified that error appears in the above-identified patent and that said Letters Patent is hereby corrected as shown below:

In the Claims

In Claim 1, Column 21, Line 50, replace "ae" with "are" prior to 'operably'.

Signed and Sealed this
Third Day of December, 2024

Katherine Kelly Vidal
*Director of the United States Patent and Trademark Office*